US010379609B2

(12) United States Patent
Nagamatsu et al.

(10) Patent No.: US 10,379,609 B2
(45) Date of Patent: Aug. 13, 2019

(54) LINE-OF-SIGHT MEASUREMENT DEVICE, LINE-OF-SIGHT MEASUREMENT METHOD AND LINE-OF-SIGHT MEASUREMENT PROGRAM

(71) Applicant: NATIONAL UNIVERSITY CORPORATION KOBE UNIVERSITY, Kobe-shi, Hyogo (JP)

(72) Inventors: Takashi Nagamatsu, Hyogo (JP); Tatsuhiko Ueki, Hyogo (JP)

(73) Assignee: National University Corporation Kobe University, Hyogo (JP)

( * ) Notice: Subject to any disclaimer, the term of this patent is extended or adjusted under 35 U.S.C. 154(b) by 448 days.

(21) Appl. No.: 14/891,578

(22) PCT Filed: May 22, 2014

(86) PCT No.: PCT/JP2014/002707
§ 371 (c)(1),
(2) Date: Nov. 16, 2015

(87) PCT Pub. No.: WO2014/188727
PCT Pub. Date: Nov. 27, 2014

(65) Prior Publication Data
US 2016/0086338 A1    Mar. 24, 2016

(30) Foreign Application Priority Data

May 22, 2013    (JP) .................. 2013-108441

(51) Int. Cl.
*H04N 7/18*    (2006.01)
*H04N 9/47*    (2006.01)
(Continued)

(52) U.S. Cl.
CPC .............. *G06F 3/013* (2013.01); *B60K 35/00* (2013.01); *G02B 27/0093* (2013.01);
(Continued)

(58) Field of Classification Search
CPC .......... G06T 7/0044; G06T 7/80; A61B 3/113
See application file for complete search history.

(56) References Cited

U.S. PATENT DOCUMENTS 7,533,989 B2 * 5/2009 Ebisawa ............ G06K 9/00604
351/208
8,493,390 B2   7/2013 Kalinli
(Continued)

FOREIGN PATENT DOCUMENTS

JP    2007-136000 A    6/2007
WO   2012/020760 A1   2/2012
WO   2012/077713 A1   6/2012

OTHER PUBLICATIONS

International Search Report translation, PCT/JP2014/002707, dated Nov. 27, 2014, 1 page.
(Continued)

*Primary Examiner* — Girumsew Wendmagegn
(74) *Attorney, Agent, or Firm* — Ogilvie Law Firm (57) ABSTRACT

Provided are a line-of-sight measurement device and method, which perform automatic calibration of line-of-sight measurement for distance-gazing users. The device is provided with: an optical axis-calculating means for calculating the optical axes of both the left and right eyeballs when viewing two distant points; a discrepancy calculating means for calculating, with the visual axes of the left and right eyeballs during distance-gazing being parallel as a constraint, the discrepancies between the optical axes and the visual axes for both the left and right eyeballs; and a fixation point-calculating means for calculating the user's fixation point on the basis of the discrepancy between the optical axes and the visual axes. For the constraint, the outer product value of the respective vectors of the left and right
(Continued)

eye visual axes is 0 or the inner product of the respective unit vectors of the left and right eye visual axes is 1.

17 Claims, 5 Drawing Sheets

(51) Int. Cl.
*G06F 3/01* (2006.01)
*B60K 35/00* (2006.01)
*G08B 21/06* (2006.01)
*G06K 9/00* (2006.01)
*H04N 5/225* (2006.01)
*H04N 5/247* (2006.01)
*G06T 7/80* (2017.01)
*G06T 7/73* (2017.01)
*G02B 27/00* (2006.01)
*A61B 3/113* (2006.01)
*A61B 5/18* (2006.01)
*G02B 27/01* (2006.01)

(52) U.S. Cl.
CPC ............ *G06K 9/00604* (2013.01); *G06T 7/74* (2017.01); *G06T 7/80* (2017.01); *G08B 21/06* (2013.01); *H04N 5/2256* (2013.01); *H04N 5/247* (2013.01); *A61B 3/113* (2013.01); *A61B 5/18* (2013.01); *G02B 2027/014* (2013.01); *G06T 2207/30201* (2013.01)

(56) References Cited

U.S. PATENT DOCUMENTS

| | | |
|---|---|---|
| 8,510,166 B2 | 8/2013 | Neven |
| 8,553,936 B2 | 10/2013 | Fogt |
| 8,562,136 B2 | 10/2013 | Blixt et al. |
| 8,710,986 B2 | 4/2014 | Tsou |
| 8,730,266 B2 | 5/2014 | Brown et al. |
| 8,885,877 B2 | 11/2014 | Publicover et al. |
| 8,929,589 B2 | 1/2015 | Publicover et al. |
| 8,994,654 B2 | 3/2015 | Lee et al. |
| 9,179,833 B2 | 11/2015 | Narasimha-Iyer et al. |
| 2014/0085189 A1* | 3/2014 | Shimasaki ............ G06F 3/013 345/156 |

OTHER PUBLICATIONS

Guestrin, E.D.,M. Eizenman, "General Theory of Remote Gaze Estimation Using the Pupil Center and Corneal Reflections", IEEE Transactions on Biomedical Engineering, vol. 53, No. 6, Jun. 2006, pp. 1124-1133 (annotations are not necessarily from inventors).

Shih, S.-W.,J. Liu, "A Novel Approach to 3-D Gaze Tracking Using Stereo Cameras", IEEE Transactions on Systems, and Cybernetics, vol. 34, No. 1, Feb. 2004, pp. 234-245.

Nagamatsu, T., J. Kamahara, N. Tanaka, "3D Gaze Tracking with Easy Calibration Using Stereo Cameras for Robot and Human Communication", Proceedings of the 17th IEEE International Symposium on Robot and Human Interactive Communication, Technische Universität Munchen, Munich, Germany, Aug. 1-3, 2008, pp. 59-64.

Nagamatsu, T., T. Ueki, J. Kamahara, "Automatic user-calibration method for gaze tracking system by looking into the distance", IEICE Technical Report, vol. 113, No. 3, May 23, 2013, pp. 65-68 plus bibliographic material for 6 pages total.

* cited by examiner

LINE-OF-SIGHT MEASUREMENT DEVICE, LINE-OF-SIGHT MEASUREMENT METHOD AND LINE-OF-SIGHT MEASUREMENT PROGRAM

TECHNICAL FIELD

The present invention relates to a line-of-sight measurement of a user who gazes mainly a distant place, for example a user who gazes a distant place from an observation tower and also a line-of-sight measurement on operators of trains, cars and ships and further relates to a line-of-sight measurement being automatically calibrated under a situation for a user gazing a distant place.

BACKGROUND ART

Conventionally, there has been a non-contact line-of-sight interface as one kind of interface for operating a computer. This line-of-sight interface detects a line-of-sight of a user as data by using a camera and a light source and operates icons and such on a computer screen by using the detected line-of-sight data. This line-of-sight interface films an eyeball while irradiating a light from a light source such as an infrared light on the eyeball and consequently detects direction data calculated from a reflected light such as an infrared light of a filmed image at a cornea surface as estimated line-of-sight data.

A different error for each user is generated between estimated line-of-sight data calculated by this technology and a real line-of-sight data by an actual user. The source for causing an error includes various elements such as an individual difference in an eyeball shape, optical refraction at a corneal surface, an individual difference regarding the position of fovea centralis and so on.

Therefore, a compensation parameter for each user is previously calculated in the aim to compensate an error in estimated line-of-sight data in regard to real line-of-sight data and a process called calibration performed by this compensation parameter on the estimated line-of-sight thus calculated is conducted.

The calibration processing is conducted by using a compensation parameter calculated from the difference between the actual direction data from an eyeball to each marker and the estimated line-of-sight data detected by having users gaze predetermined plural markers in turn and consequently detecting the estimated line-of-sight data when each marker is gazed at.

It becomes possible to detect direction data closer to an actual user gaze as line-of-sight data by conducting the calibration processing.

However, it is necessary to let a user gaze about five to twenty markers when a compensation parameter is generated for detecting high precision line-of-sight data and consequently user's burden was heavy. Under such a circumstance, a technology to decrease the calibration process to a one point marker is disclosed. (Refer to a patent literature 1 and non-patent literatures 1 to 3, for example.)

These techniques find an optical axis of an eyeball, which is an axis connecting a center of curvature of a cornea and a pupil center of a pupil from eyeball images by filming a reflected light out of a light source at a cornea surface and a pupil. And a discrepancy (including individual differences) between an optical axis of an eyeball and a visual axis (equivalent to a line-of-sight) is found by a calibration that gazes one point and consequently a line-of-sight is correctly found with shifting of the optical axis measured by a quantity of discrepancy. Because the position of fovea centralis inside an eyeball cannot be filmed by a camera from outside according to these technologies, it is difficult to reduce the number of point to be gazed at the time of calibration from one point.

The inventors of the present invention already proposed line-of-sight measurement equipment that does not require a calibration processing because of a constraint condition in which visual axes intersect on a display screen after measuring the optical axes of both eyeballs. (Refer to the patent literature 2)

The line-of-sight measurement device the inventors of the present invention propose is a measurement device that acquires an eyeball image by the reflected light out of a light source concerning a user watching a display screen using a camera, calculates an optical axis which is an axis connecting a center of curvature of a cornea and a pupil center of a pupil from eyeball images, then calculates a discrepancy between an optical axis and a visual axis being an axis connecting a fovea centralis and a center of curvature of a cornea by using the calculated optical axis, finds the visual axis by shifting the optical axis based on the discrepancy between the optical axis and the visual axis and calculates the user's fixation point on the screen as a cross point of the display and the visual axis.

Figure 1:
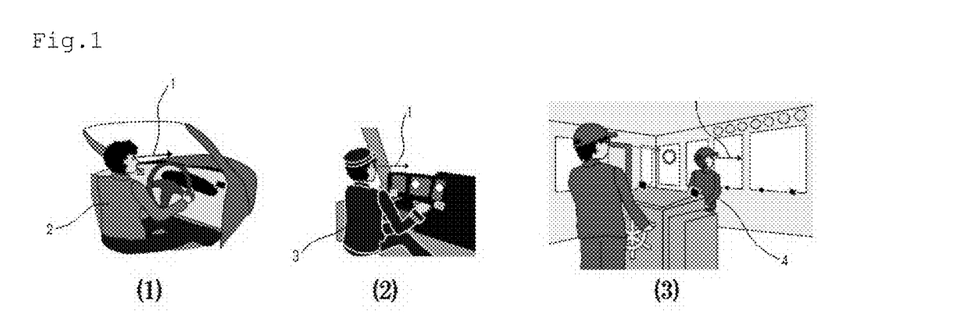
FIG. 1 An explanatory figure of the line-of-sight at vehicles, (1) the line-of-sight of a car driver, (2) the line-of-sight of a train operator and (3) the line-of-sight of a ship captain FIG. 2 A schematic figure of the rotation of an eyeball FIG. 3 An explanatory figure of the rotation of optical axis and visual axis of an eyeball FIG. 4 A functional block diagram of the line-of-sight measurement device according to embodiment 1

On the other hand, when situations wherein a line-of-sight measurement is conducted for users who gaze in a long distance at operation of vehicles such as cars, trains and ships or a user who gazes in a long distance from an observation platform, not an interface for operating computers, are supposed as shown in FIG. 1, it is thought that users gaze somewhere in a long distance in the forward direction for most of the time. The arrow 1 in FIG. 1 shows the line-of-sight of an automobile driver 2, the line-of-sight of a train-operator 3 and the line-of-sight of a ship captain 4.

It would be very idealistic, regarding this kind of users, if a calibration is conducted naturally during visual line movement of gazing in a long distance without gazing somewhere specifically designated.

According to the technologies disclosed by the patent literature 1 and non-patent literatures 1 to 3 as mentioned above, there is a constraint such as the subject must gaze at least one predetermined point. Even under such a constraint, a calibration only for once at the first time would enough if an individual can be specified, however it would not be suitable for the case wherein unspecified large number of people were supposed to be measurement objects.

Also, according to the technology disclosed in the patent literature 2, automatic calibration is possible for a case wherein a display screen is gazed at, however in the case of operations of vehicles such as cars, trains and ships, the technology is not adequate because the time duration for the operators to gaze the nearby displays and so on is very short and the operators gaze at somewhere in the distance most of the time. Also, there is such a problem that one of the technologies disclosed in patent literature 2 utilizing the middle point of an intersection of optical axes of both eyeballs and a display can perform an automatic calibration within an instant (one frame), however precision of this technology becomes lower than that of the technology accompanied by a calibration with a close observation.

Furthermore, a technology for detecting a gaze direction is known (Refer to parent literature 3) by displaying a target on a virtual image surface in the forward direction of an operator using a head-up display for the operator to gaze. However, the calibration is conducted by using a target to be easily gazed at in this case, not by an automatic calibration during a natural visual line movement of a user.

Also, with regard to car driving, all the people do not necessarily own a car of themselves and a family member or a friend could drive that car. There could be an operator change during train operation and different person could operate. With regard to a ship, a plurality of persons exists in the bridge simultaneously and also there is a shift. Also, a possibility that an unexpected person operates and navigates the ship due to sudden illness cannot be denied. For this kind of circumstance, a technology that enables an automatic calibration is desired for the purpose of using a line-of-sight measurement device at all times as a safety device even under an operation by a user other than a designated user.

PRIOR ART

Patent Literature

[Patent literature 1] JP 2007-136000 A
[Patent literature 2] JP 2009-297323 A
[Patent literature 3] JP 2009-183473 A Non-Patent Literature

[Non-patent literature 1] Guestrin, E. D., M. Eizenman: General Theory of Remote Gaze Estimation Using the Pupil Center and Corneal Reflections, IEEE Transactions on Biomedical Engineering, Vol. 53, No. 6, pp. 1124-1133 (2006).
[Non-patent literature 2] Shih, S.-W., J. Liu: A novel approach to 3-D gaze tracking using stereo cameras, IEEE Transactions on Systems, Man, and Cybernetics, Part B, Vol. 34, No. 1, pp. 234-245 (2004).
[Non-patent literature 3] Nagamatsu, T., J. Kamahara, N. Tanaka: 3D Gaze Tracking with Easy Calibration Using stereo Cameras for Robot and Human Communication, in Proceedings of the 17th International Symposium on Robot and Human Interactive Communication (IEEE RO-MAN) 2008, pp. 59-64. (2008).

OUTLINE OF THE INVENTION

Problems to be Solved by the Invention

In view of the circumstances described above, the present invention aims to provide a line-of-sight measurement device and a method thereof for conducting a line-of-sight measurement of a user gazing in a long distance including users who gaze in a long distance from an observation platform and operators of trains, cars, ships and so on, by an automatic calibration.

Means to Solve the Objects

In order to attain the goal mentioned above, the line-of-sight measurement device according to the present invention, being a line-of-sight measuring device for users who gaze mainly in the distance, is equipped with an optical axis calculating means for calculating the eyeball axes of both right and left eyeballs when gazing at least two points in the distance, a discrepancy calculation means for calculating a discrepancy between the optical axis of the left eyeball and the visual axis of the left eyeball, and a discrepancy between the optical axis of right eyeball and the visual axis of the right eyeball, under a constraint condition that the visual axes (the line-of-sight) of both left and right eyeballs are parallel to each other when gazing in the distance and a gaze point calculation means for calculating the gaze point of the user.

By the configuration mentioned above, a line-of-sight measurement for a user mainly gazing in the distance is performed not with a calibration by a conscious gaze at a predetermined fixation point, but with an automatic calibration by a natural gaze in the distance. Namely, discrepancies between the optical axes and the visual axes of both left and right eyeballs can be calculated by calculating optical axes of both left and right eyeballs gazing at two or more points in the distance under a constraint condition that the visual axes (the-lines-of sight) of user's left and right eyeballs when the user gazes in the distance are parallel. For that reason, the calibration for a user to gaze at a predetermined marker beforehand is not necessary because an automatic calibration can be performed.

Note that "the calibration" means have the same meaning as "find the discrepancy between the optical axis and the visual axis" in the present specification.

Here, the user who gazes mainly in the distance means a user who gazes in the distance at an observation platform or an operator at an operation of transport vehicles including trains, cars and ships. In addition, operators of training simulation equipment for operation trainings of vehicles such as trains, cars, ships, airplanes, bicycles and so on are included. The present invention can be preferably employed to line-of-sight measurements of operators who operate actual vehicles and line-of-sight measurements of operators for training simulation equipment of operation training. In the case of simulation equipment, there is a possibility that the operator of the simulation equipment can be treated as a user who gazes in the distance by employing a device that displays an image at an infinite distance by using a special optical system, although the projection screen is possibly located at distance of several meters. The present invention can be preferably employed also to line-of-sight measurements of a user who gazes at a distance at an observation platform.

A constraint condition that the visual axes (line-of-sight) of user's left and right eyeballs are parallel to each other is employed because the line-of-sights of the users at an observation platform for gazing a distance and operators (users) of trains, cars and ships during operation mainly gaze in the distance.

In the case where automatic calibration is performed by gazing at 2 points or more in the distance, the discrepancy between an optical axis and a visual axis is calculated by assessing variables for expressing the discrepancy between the optical axis and the visual axis of the eyeball by setting a constraint that the each unit vector of the visual axes of both left and right eyeballs.

Also, in the case where an automatic calibration by gazing at least 4 points in the distance is performed, the 4 variables for expressing the discrepancies between the optical axes and the visual axes of both left and right eyeballs are assessed either by the outer product value of the vector of each visual axis of both left and right eyeballs or by forming an equation of an inner product of a unit vector, as will be explained later. The reason the expression "at least" is used is that the calculation accuracy becomes higher with higher number of measurement points because noises are usually included when a characteristic is extracted from an image filmed by a camera for example, to be calculated for computation of the eyeball optical axis.

In the case where optical axis calculation means calculates optical axes of both left and right eyeballs when at least 4 points in the distance are gazed, the constraint condition is either the outer product value for each vector of visual axes of both left and right eyeballs equals 0 or the inner product of each unit vector of visual axes of both left and right eyeballs equals 1. Employment of a numerical formula easily realizes arithmetic processing using a computer.

The constraint condition satisfies the numerical formula (1) below against the eyeball optical axes of both left and right eyeballs when at least 4 points in the distance are gazed, in a case where the inner product of each unit vector for the visual axes of left and right eyeballs equals 1. Note that each $c_{Ln}(\alpha_L, \beta_L)$ and $c_{Rn}(\alpha_R, \beta_R)$ are unit vectors of the visual axes of left and right eyeballs, and are expressed as a function of the horizontal discrepancy angle $\alpha$ and the vertical discrepancy angle $\beta$ each from the optical axis. Also note that L denotes left, R denotes right and n is 0, 1, - - - , N (N is more than 3).

(Formula 3)

$$c_{Ln}(\alpha_L,\beta_L) \cdot c_{Rn}(\alpha_R,\beta_R)=1 \quad \text{(Equation 1)}$$

This is because the unit vector of the visual axis of both left and right eyeballs is expressed as a function of the horizontal discrepancy angle $\alpha$ and the vertical discrepancy angle $\beta$ each from the optical axis. Regarding this will be explained later.

Also, the constraint condition satisfies the numerical equation (2) below against the eyeball optical axes of both left and right eyeballs when at least 4 points in the distance are gazed, in the case where the outer product value of each unit vector for the visual axes of left and right eyeballs equals 0. Note that each $c_{Ln}(\alpha_L, \beta_L)$ and $c_{Rn}(\alpha_R, \beta_R)$ are unit vectors of the visual axes of left and right eyeballs, and are expressed as a function of the horizontal discrepancy angle $\alpha$ and the vertical discrepancy angle $\beta$ each from the optical axis. Also note that L denotes left, R denotes right and n is 0, 1, N (N is more than 3). Further, the left side of the numerical equation (2) below is enclosed in double vertical lines because it expresses the size (norm) of the vector.

(Formula 4)

$$\|c_{Ln}(\alpha_L,\beta_L) \times c_{Rn}(\alpha_R,\beta_R)\|=0 \quad \text{(Equation 2)}$$

Also, the optical axis calculation means calculates the optical axis which is an axis linking the center of the curvature of the cornea or the rotation center of the eyeball and the pupil center of an pupil, from an eyeball image which is an image of an eyeball regarding a user who gazes in the distance. Here, the eyeball image is preferably an image of an eyeball formed by the light out of a specified light source, reflected at the eyeball.

In order to acquire an image of an eyeball by the light out of a specified light source, the light being reflected at the eyeball, as an eyeball image, the line-of-sight measurement device according to the present invention comprises at least two camera means each disposed at each different position for acquiring eyeball images of both left and right eyeballs, and at least two light source means disposed at each different position so that the reflected light source images at the eyeballs are separated to each other, in front of the user. And at least two Purkinje images are formed within a region where the radius curvature of the cornea of the eyeballs of the left and right eyeballs is constant, and the position of the Purkinje image of the light source means at the eyeball image filmed by either one of the light source means and the position of the actual light source means are matched and the optical axis of the eyeball is calculated from positional relations of at least 2 matched sets of camera means and light source means.

Also, at the discrepancy calculation means mentioned above, the discrepancy angle converges by setting a constraint where the search range of discrepancy angle for the visual axis against the light axes of left and right eyeballs is made to be less than ±7° in the horizontal direction and ±2° in the vertical direction. This arrangement secures the stability of the solution of the discrepancy angle. The reason for setting ±7° in the horizontal direction and ±2° in the vertical direction is based on the fact that the optical axis of an eyeball and the actual human line-of-sight is known to be shifted by about 5° in the horizontal direction and about 1° in vertical direction in average. Note that the magnitude and the direction of the discrepancy is individually different but there are few cases where the discrepancy is remarkably larger than ±7° in horizontal direction and ±2° in vertical direction and accordingly the search range is set at the predetermined range as mentioned above by giving priority to stability of the solution.

Also, the line-of-sight measurement method according to the present invention is a line-of-sight measurement method for users who gaze mainly in the distance and is comprised of an optical axis calculation step for calculating eyeball optical axes of both left and right eyeballs when gazing at least 2 points in the distance, a calculation step for calculating the a discrepancy between the optical axis of the left eyeball and the visual axis of the left eyeball, and a discrepancy between the optical axis of right eyeball and the visual axis of the right eyeball, under the constraint condition of line-of-sight axes (visual axes) being in parallel under a gaze in the distance and the fixation point calculation step for calculating the fixation point of a user based on the discrepancy between the optical axis and the visual axis. In a case where the optical axes of both left and right eyeballs are calculated when gazing at least 4 points in the distance by the above mentioned optical axis calculation step, the constraint condition is either the outer product value for each vector of visual axes of both left and right eyeballs is 0 or the inner product of unit vector of each visual axes of both left and right eyeballs is 1.

Also, the line-of-sight measurement program according to the present invention is the line-of-sight measurement program for users who mainly gaze in the distance, letting a computer execute the steps 1) to 3) below.

1) An optical axis calculation step for calculating optical axes of both left and right eyeballs when gazing at least 2 points in the distance;
2) A discrepancy calculation step for calculating a discrepancy between the optical axis of the left eyeball and the visual axis of the left eyeball, and a discrepancy between the optical axis of right eyeball and the visual axis of the right eyeball, under the constraint that the line-of-sight of both left and right eyeballs (visual axis) are mutually in parallel when gazing in the distance;
3) A gazing point calculation step for calculating the user's gazing point based on the discrepancy between the optical axis and the visual axis.

Effects of the Invention

According to the present invention, regarding the line-of-sight of users who gaze in the distance including operators of trains, cars, ships and so on, the line-of-sight measurement can be performed while conducting auto-calibration and accordingly there is such an effect as unidentified large number of people other than identified users can be measurement objects.

Also, according to the present invention, there is an effect that the users do not have to suffer from a burden because the calibration of gazing a specified marker by users in advance is not necessary.

By using the present invention, accidents can be prevented by operating a warning dispatches or safety devices by detecting inattentive driving by measuring the line-of-sight under the circumstances where operators of cars mainly gaze in the distance.

BEST MODE FOR CARRYING OUT THE INVENTION

According to the present invention, line-of-sight measurements of users who gaze in the distant place, including operators of trains, cars and ships, automatically find the discrepancy angle between optical axes and visual axes of both left and right eyeballs in the first place.

In order to automatically find the optical axes and visual axes of both left and right eyeballs, a constraint that the visual axes (gazes) of both left and right eye balls are in parallel while gazing in the distance is applied to automatically find the discrepancy angle between the optical axes and visual axes of both left and right eyeballs. The reason for applying this constraint is that almost all the lines-of-sight of the users under operation of trains, cars, ships and so on are supposed to be natural to originate from gazes in the distance in the front. The discrepancy between the optical axes and line-of-sight axes of both left and right eyeballs is calculated while calculating the optical axes of both left and right eyeballs by grasping the eyeball status while the eyeballs gaze at least 4 points in the distance.

By this, an automatic calibration becomes possible by calculating the discrepancy between the optical axes and visual axes of both left and right eyeballs using a natural state of user's gaze, without calibration processing for a user to gaze a specified marker in advance.

And the gaze of the user can be measured because the user's gazing point afterwards can be calculated by finding the discrepancy between optical axes and visual axes. Regarding the gazing points afterwards, the gazing points nearby such as the ones on the meter panels, not only the gaze points in the distance, can be calculated.

First, before explaining the line-of-sight measurement device and the method according to the present invention, the rotation of eyeballs that follows the Listing's law is explained.

The eyeballs usually function following a certain fixed rule, not functioning in all the practicable ways in their function. This certain fixed rule is called Listing's law. The Listing's law is a law regarding rotational movement and position of eyes referring to a law of eyeball movement, which are (a) an arbitrary eye position takes only those positions that can be attainable by only a single rotation from the primary position of the eyeball, and (b) the rotational axis of the rotation exists in a plane vertical to the visual axis direction of the Primary position (listing plane). Note that the Primary Position is an eye position relative to a head, satisfying the Listing's law and gazing in the direction horizontal and forward under the situation that the user stands almost upright.

Figure 2:
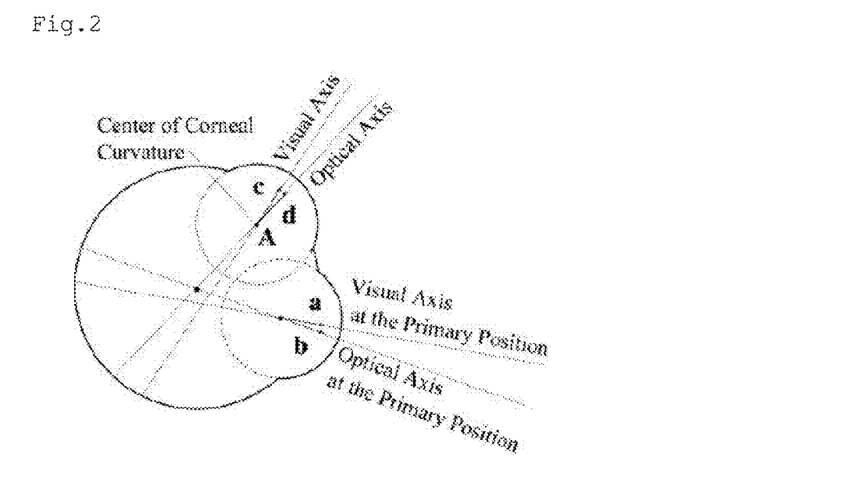

The relationship between the visual axis and the optical axis at the primary position of the eyeball before an eye ball movement and the eye position after an eye ball movement is shown in FIG. 2. In the FIG. 2, a, b are a visual vector and an optical axis vector of the eyeball at the primary position, respectively and c, d are a visual vector and an optical vector after rotation, respectively. Each vector is a unit vector. And A represents the corneal center of curvature of an eyeball. Here, a, b, c, d, A are printed in a bold typeface to show that these represent vectors. In this specification, alphabetical printing is printed in the following manner where alphabetical capital letters (bold typeface) represent a position vector and alphabetical small letters (bold typeface) represent a unit direction vector.

Note that the eye position after the eye movement includes the eyeball position (the secondary position of the eyeball) when an eyeball is rotated vertically or horizontally from the primary position and the eyeball position (the tertiary position of the eyeball) when eyeball is rotated in a way other than rotationally or horizontally from the primary position. In FIG. 2, the unit direction vector of the visual axis at the primary position is represented by a (the first visual axis vector), the unit direction vector of the optical axis at the primary position is represented by b (the first optical axis vector), the unit direction vector of the optical axis at the eyeball position after the eyeball movement is represented by c (the second visual axis vector) and the unit direction vector of the optical axis at the eyeball position after the eyeball movement is represented by d (the second optical axis vector).

The first visual axis vector a is a vector of the direction of a forward gazing when a person stands almost upright, also a vector to change according to the position of the head, which is relatively determined by the position of the head. The first visual axis vector a the direction thereof is known based on some reason such as approximating with the direction of the front.

Figure 3:
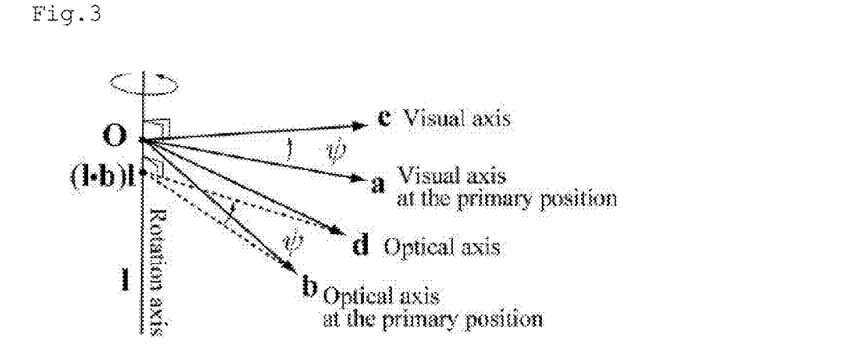

Next, the relationship between the visual axis and the optical axis at the primary position based on the Listing's law and the eye position after the eye movement is shown in FIG. 3. In FIG. 3, each vector a, b, c, d in FIG. 2 is moved to congregate each start point in one place so that the rotational correlation can be clearly understood. In FIG. 3, the rotation axis when the eyeball is moved directly from the primary position to the eye position after the movement is represented by l. l is a unit directional vector along the rotation axis of the eyeball and the eyeball takes only those positions that are rotated around the axis within the listing plane vertical to a (the directional vector of an axis is l) from a which is the primary position. When the eyeball is rotated by an angle ψ from the primary position to reach the eye position after the movement, the first visual axis vector a is rotationally moved by an angle ψ to become the second visual axis c and the first optical axis vector b is rotationally moved by an angle ψ to become the second optical axis vector d. At this instant, the rotational axis l exists within the listing plane vertical to the first visual axis vector a. In more detail, the rotation axis l becomes vertical to the first visual axis vector a and the second visual axis vector c.

Here, the first optical axis vector b, which is a vector in the 3 dimensional space, can be expressed by the 3 variables that are the value (x) on the X axis, the value (y) on the Y axis and the value (z) on the Z axis and by defining the first optical axis vector b as a unit vector, the condition of $x^2+y^2+z^2=1$ is added and Z becomes known when X and y are known, accordingly.

The rotation axis l and the rotation angle ψ can be calculated by the equations (3) and (4) below from the first optical axis vector b and the second optical axis vector d.

(Equation 5)

$$l = \frac{a \times (d-b)}{\|a \times (d-b)\|} \quad (3)$$

(Equation 6)

$$\psi = \arccos\left(\frac{(b-(l \cdot b)l) \cdot (d-(l \cdot b)l)}{\|b-(l \cdot b)l\|\|d-(l \cdot b)l\|}\right) \quad (4)$$

The second visual vector c can be calculated by rotating the first visual vector a around the rotation axis l by an angle ψ. Namely, c can be found when a is rotated as expressed in the equation (5) below. Here, R (ψ, l) is a matrix that rotates by ψ around the axis l.

(Equation 7)

$$c = R(\psi, l)a \quad (5)$$

The rotation of an eyeball obeying the Listing's law has been explained thus far.

Below, the embodiment of the present invention will be explained in detail referring to the figures. Note that the range of the present invention is not limited to the following embodiments and figures but many changes and transformation can be applicable.

Embodiment 1

Figure 4:
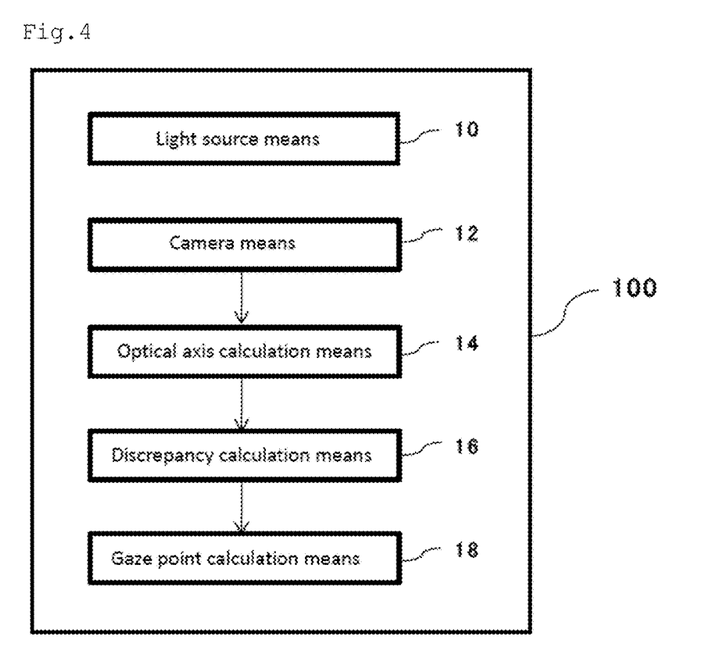

The embodiment of the line-of-sight measurement device according to the present invention will be explained using a functional block diagram as shown in FIG. 4. The line-of-sight measurement device 100 comprises of 5 components that are a light source means 10, a camera means 12, an optical axis calculation means 14, a discrepancy calculation means 16 and a gaze point calculation means 18. Here, the optical axis calculation means is a means for calculating the optical axis of users' eyeball and can be any means as long as the means can routinely calculate the optical axis of an eyeball using a known method. In the embodiment here, a method employing 2 cameras and 2 light sources for one eye is employed. By this arrangement, the optical axis of an eyeball can be found accurately and speedily (within 1 frame).

2 LED light sources (a LED light source which irradiates infrared light is employed) disposed at the front and all the surrounding area of a user and a camera for acquiring an eyeball image by a reflection light emitted from a LED light source (in a case where the LED light source emits an infrared light, an infrared camera having sensitivity to infrared light) is prepared.

Although it would be good enough for two cameras to film both the eyes, 2 cameras for the right eye and 2 cameras for the left eye, the total of 4 cameras are used to film an eyeball with a high resolution.

Figure 5:
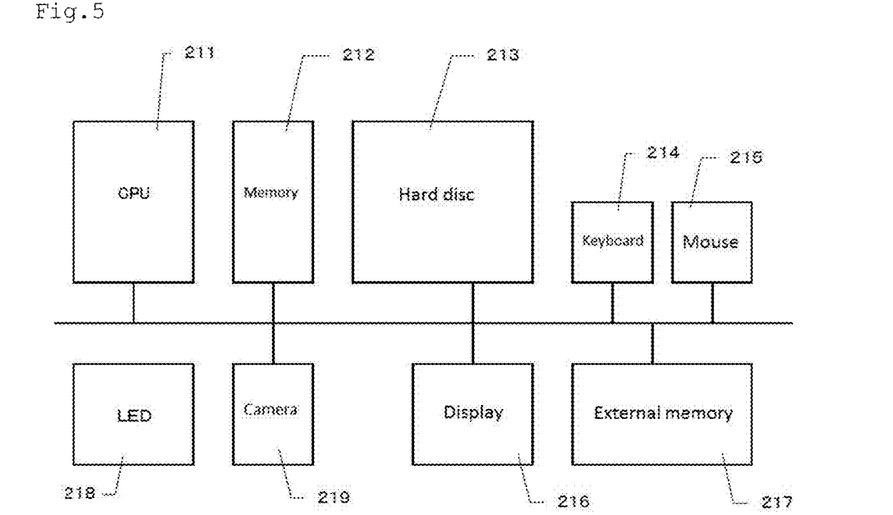
FIG. 5 A system configuration figure of the line-of-sight measurement device according to embodiment 1

The hardware configuration of a line-of-sight measurement device is explained referring to FIG. 5. The line-of-sight measurement device 100 is furnished with a CPU 211, a memory 212, a hard disc 213, a keyboard 214, a mouse 215, a display 216, an external memory 217, LEDs 218 and cameras 218.

The CPU 211 works on processing based on the operating system (OS) stored in the hard disc 213 and other application programs such as a line-of-sight measurement program. The memory 212 provides a work area to the CPU 211. The hard disc 213 records and holds an operating system (OS), the line-of-sight measurement program and other application programs and measurement data obtained as a result of line-of-sight measurements.

A keyboard 214 and a mouse 215 receive commands from outside. A display 216 displays eyeball images of subjects filmed by cameras 219 that are 2 cameras for a right eye and 2 cameras for left eye, for confirmation of a user of the line-of-sight measurement device 100. An external memory 217, being a USB memory for example, reads data such as a line-of-sight measurement program.

An LED 218 irradiates light at a subject who measures a line-of-sight by the line-of-sight measurement device 100. The camera 219 films an eyeball image of the subject. In a case where 2 cameras are used, they are configured to be a stereo camera and they are used to film both eyes. Also, in a case where 4 cameras are used, 2 sets of stereo cameras are configured and they are used to film both the left and right eyes.

Figure 6:
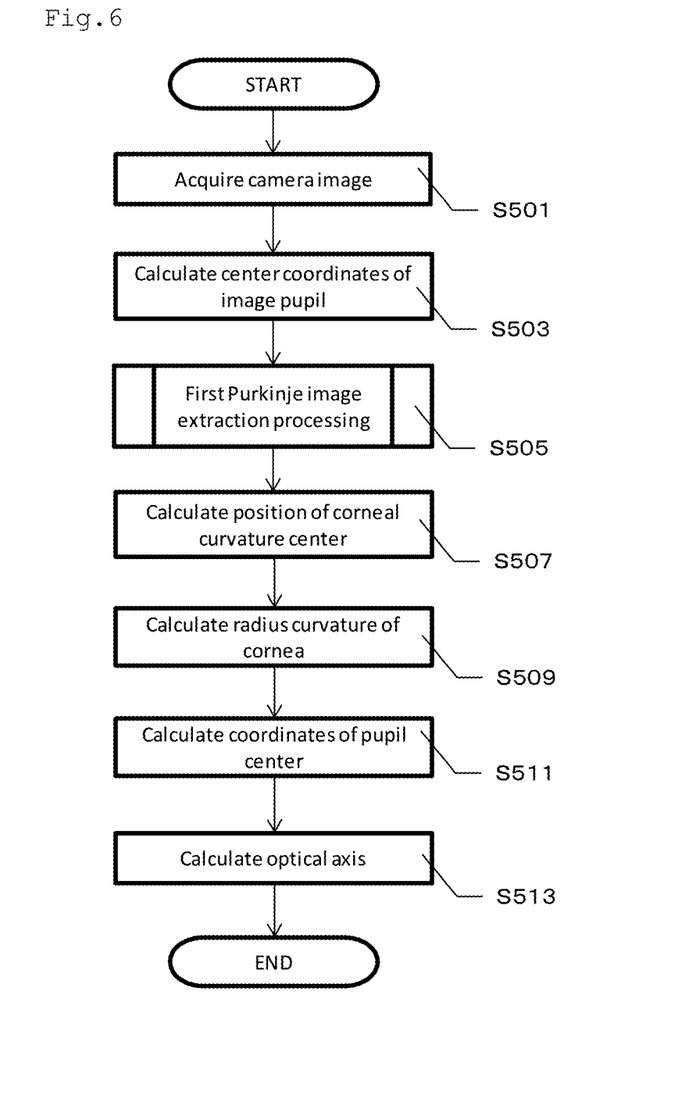
FIG. 6 A flow chart of an optical axis calculation processing for a line-of-sight measurement device FIG. 7 A flow chart of the first Purkinje image extraction processing FIG. 8 Relationship figure of an optical axis and a visual axis of both left and right eyeballs while gazing in the distance FIG. 9 An explanatory FIG. 1 of the experiment system FIG. 10 An explanatory FIG. 2 of the experiment system
Figure 7:
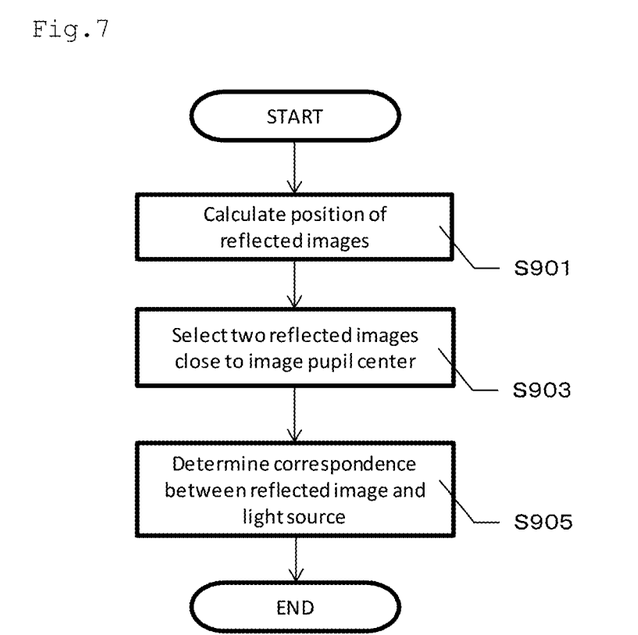

In the line-of-sight measurement device according to embodiment 1, the position of the Purkinje image of the light source on the eyeball image filmed by any one of the cameras and the position of the actual light source are correlated. And the position of the corneal curvature center is calculated by calculating a plane that includes a corneal curvature center from the camera position (lens center) and the light source position correlated with the position of the Purkinje image filmed and subsequently finding more than 3 such planes. And the central position of the pupil is calculated and then the optical axis which is an axis connecting the corneal curvature center and the pupil center of the pupil is calculated based on the position of the corneal curvature center and the position of the pupil center. Regarding the detail of above, refer to the flow chart in FIGS. 6 and 7, and also paragraphs 0019 to 0029 of the patent literature 2 described above.

According to the conventional method, the discrepancy value between the optical axis and visual axis of an eyeball was calculated in advance by a calibration operation conducted by a user beforehand, which is to gaze a predetermined place, for example. And the visual axis which is an axis connecting the fovea centralis and the corneal curvature center was calculated from the calculated optical axis using the calculated discrepancy value.

Calibration is to find the relationship between a and b in FIG. 3. Although a is relatively determined to be the position of the head, here the front is approximated to be the direction and to be already known, and subsequently the calibration becomes equivalent to estimating b.

The discrepancy between a and b is expressed by 2 variables. The horizontal discrepancy angle is assumed to be a and the vertical discrepancy is assumed to be β, b can be expressed by the equation (6) below by using α, β.

(Equation 8)

$$b = \begin{pmatrix} 1 & 0 & 0 \\ 0 & \cos\beta & -\sin\beta \\ 0 & \sin\beta & \cos\beta \end{pmatrix} \begin{pmatrix} \cos\alpha & 0 & \sin\alpha \\ 0 & 1 & 0 \\ -\sin\alpha & 0 & \cos\alpha \end{pmatrix} a. \quad (6)$$

According to the present invention, taking a view that the visual axes of both eyeballs become parallel when a user gazes in the distance, a method to conduct an automatic calibration is employed by capturing user's eyes in natural state without conducting a calibration that necessitates for a user to gaze a predetermined marker.

This will be explained below. The relationship between the optical axes and visual axes of both eyeballs is shown as in FIG. 8. The visual axes of both eyeballs become parallel. Here, the discrepancy between the optical axes and visual axes of eyeballs can be expressed by using a total of 4 variables. The 4 variables of horizontal and vertical directions of the left eye and horizontal and vertical directions of the left eye are expressed by $\alpha_L$, $\beta_L$, $\alpha_R$, $\beta_R$, respectively.

Figure 8:
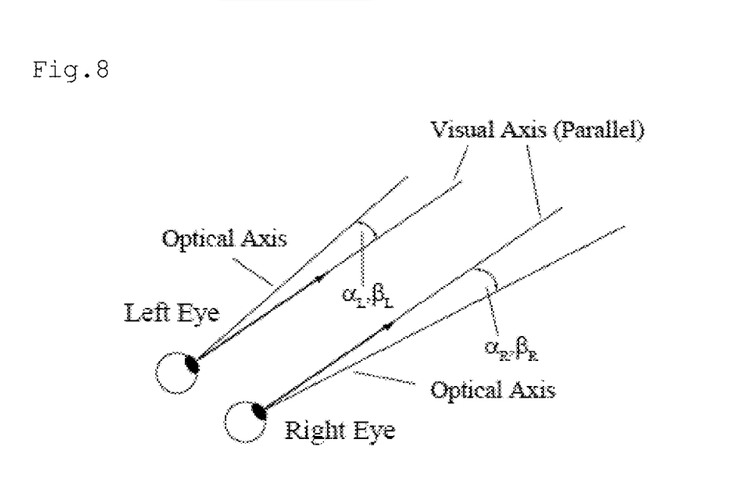

Here, let $c_L$ and $c_R$ be the visual axis of the left eye and the right eye, respectively. If $v_L$ and $c_R$ are unit vectors and parallel to each other, the inner product of $c_L$ and $c_R$ becomes 1 as shown in the equation (7) below.

(Equation 9)

$$c_L c_R = 1 \quad (7)$$

By the way, $a_L$ is known and $b_L$ can be expressed as a function of $\alpha_L$ and $\beta_L$ following the equation (6) above. $d_L$ can be found by the conventional method.

Therefore, $c_L$ can be expressed as a function of $\alpha_L$ and $\beta_L$ using equations (3) to (6) above. Similarly, $c_R$ can be expressed as a function of $\alpha_R$ and $\beta_R$.

If there are 4 unknown numbers and a user gazes 4 different directions, 4 equations would hold as expressed by the equation (8) below. By solving the 4 equations below, the 4 variables $\alpha_L$, $\beta_L$, $\alpha_R$, $\beta_R$ can be found.

(Equation 10)

$$\begin{cases} c_{L0}(\alpha_L, \beta_L) \cdot c_{R0}(\alpha_R, \beta_R) = 1 \\ c_{L1}(\alpha_L, \beta_L) \cdot c_{R1}(\alpha_R, \beta_R) = 1 \\ c_{L2}(\alpha_L, \beta_L) \cdot c_{R2}(\alpha_R, \beta_R) = 1 \\ c_{L3}(\alpha_L, \beta_L) \cdot c_{R3}(\alpha_R, \beta_R) = 1 \end{cases} \quad (8)$$

The optical axis of an eyeball is calculated by extracting characteristics from images filmed by a camera and the images usually contain noise. Therefore, the solution for the 4 variables $\alpha_L$, $\beta_L$, $\alpha_R$, $\beta_R$ are determined in such a way that the evaluation function F of the equation (9) below becomes minimum by measuring as many points as possible.

(Equation 11)

$$F(\alpha_L, \beta_L, \alpha_R, \beta_R) = \sum_i |c_{Li}(\alpha_L, \beta_L) \cdot c_{Ri}(\alpha_R, \beta_R) - 1|^2 \quad (9)$$

Next, an evaluation was conducted by using a simulation.

The simulation was conducted on 5 cases where $\alpha_L$, $\beta_L$, $\alpha_R$, $\beta_R$ of true values (True Values) were changed. The movement of an eyeball was calculated for 25 directions in the range −20° to 20° with a 10° pitch in both horizontal and vertical directions. Data of 60 points for each direction was prepared by adding errors originating to measurement so that the standard deviation becomes 0.3°. The intensity of the measurement error was determined to be 0.3° based on the result that the measurement of the optical axis of the eyeball by the conventional method provided horizontally 0.21° and vertically 0.18°.

As mentioned above, data represented by median in each direction for 25 directions were prepared by using simulated data of measurement result on the optical axis of an eyeball and such data was used to find $\alpha_L$, $\beta_L$, $\alpha_R$, $\beta_R$ that make the equation (9) above minimum. This was repeated 5 times for each case and the average (ave.) and the standard deviation (SD) for that 5 times were calculated.

The result is shown in table 1 below.

The table below shows that $\alpha_L$, $\beta_L$, $\alpha_R$, $\beta_R$ can be calculated correctly and the SD is small when |α| of cases 1 to 4 are large (in the case where discrepancy angle is 3° and 5°). On the other hand, when |α| is small (the discrepancy angle is 1°) as in the cases 5,6, $\alpha_L$, $\beta_L$, $\alpha_R$, $\beta_R$ are not found very correctly and the SD is known to vary greatly.

TABLE 1

| | | Degrees | | | |
|---|---|---|---|---|---|
| Case | | $\alpha_L$ | $\beta_L$ | $\alpha_R$ | $\beta_R$ |
| 1 | True value | −5.00 | 1.00 | 5.00 | 1.00 |
| | Proposed method (ave.) | −5.08 | 1.16 | 4.92 | 1.16 |
| | Proposed method (SD) | 0.25 | 0.38 | 0.25 | 0.37 |
| 2 | True value | −5.00 | −1.00 | 5.00 | −1.00 |
| | Proposed method (ave.) | −5.00 | −0.97 | 5.00 | −0.97 |
| | Proposed method (SD) | 0.32 | 0.22 | 0.31 | 0.22 |
| 3 | True value | −3.00 | 1.00 | 3.00 | 1.00 |
| | Proposed method (ave.) | −3.39 | 0.66 | 2.61 | 0.67 |
| | Proposed method (SD) | 0.33 | 0.56 | 0.33 | 0.56 |
| 4 | True value | −3.00 | −1.00 | 3.00 | −1.00 |
| | Proposed method (ave.) | −3.01 | −1.08 | 2.98 | −1.08 |
| | Proposed method (SD) | 0.33 | 0.51 | 0.33 | 0.50 |
| 5 | True value | −1.00 | 0.50 | 1.00 | 0.50 |
| | Proposed method (ave.) | −0.77 | −0.01 | 1.23 | −0.01 |
| | Proposed method (SD) | 1.75 | 1.05 | 1.74 | 1.05 |
| 6 | True value | −1.00 | −0.50 | 1.00 | −0.50 |
| | Proposed method (ave.) | 0.01 | −0.88 | 2.01 | −0.87 |
| | Proposed method (SD) | 1.07 | 1.75 | 1.06 | 1.75 |

When the discrepancy between the optical axis and visual axis of an eyeball is large, the discrepancy can be found correctly by using the present invention. However, when the discrepancy between the optical axis and the visual axis of an eyeball is small, the discrepancy cannot correctly found as a result because the influence of noise becomes larger and the calculation results become unstable in the calculation process of finding the discrepancy. However, in a case where the discrepancy between the optical axis and visual axis of an eyeball is small, the optical axis may be approximated to be the visual axis. There is a possibility to find which case should be selected after finding out the extent of variance after the calculation is performed for several times.

Figure 9:
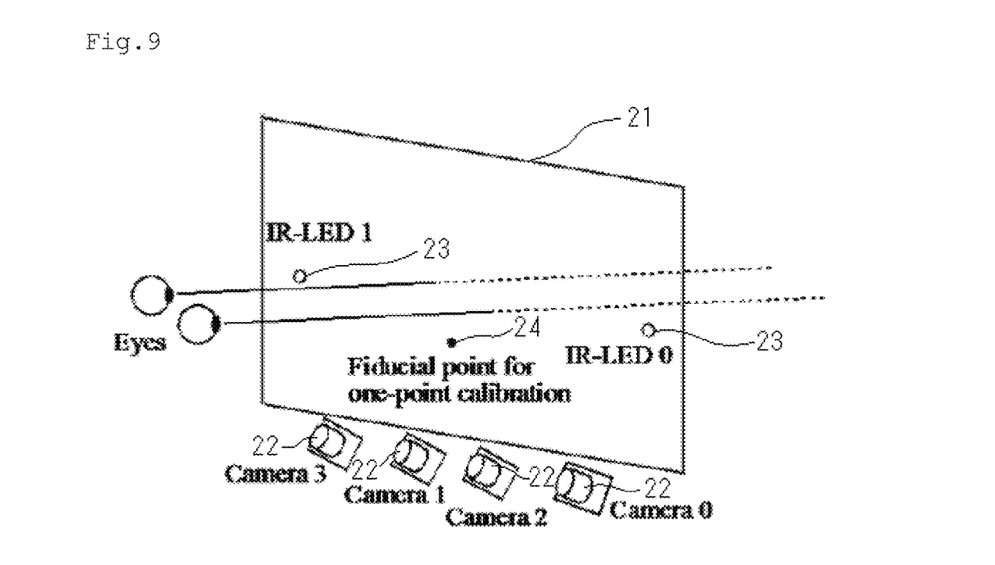
Figure 10:
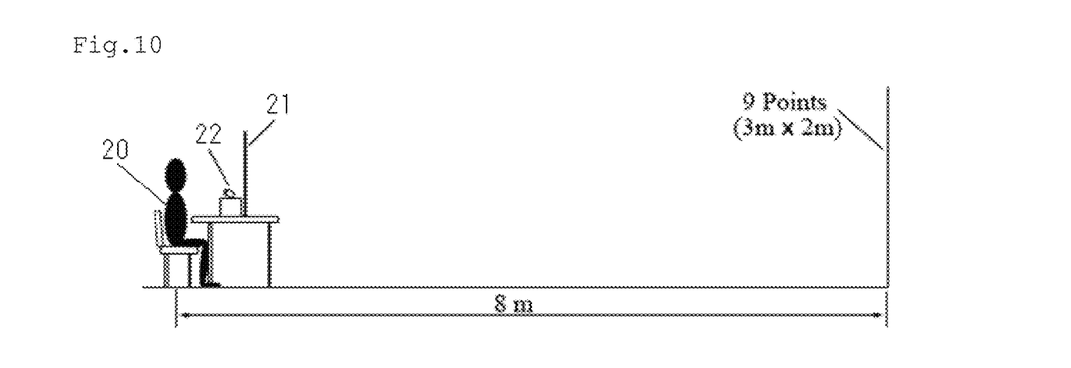

Next, the accuracy of the line-of-sight measurement device was evaluated by constructing an experimental system as shown in FIGS. 9 and 10.

The experimental system is constructed with 4 cameras 22 (Camera 0 to Camera 3) disposed at a sill of a glass plate 21 to acquire images of eyeballs of a subject 20 who is asked to gaze a target in the distance through a glass plate 21 in the front. Two infrared LED's (IR-LED) 23 are disposed at the glass 21. Also, a marker 24 for 1 point calibration to find $\alpha_L$, $\beta_L$, $\alpha_R$, $\beta_R$ by the 1 point calibration method which belongs to a prior art is disposed on the glass plate 21. (Refer to the non-patent literature 3 described above to find out about the 1 point calibration method.)

The subject is asked to gaze a target made of 9 points in the front by 8 meters through a glass plate 21.

The optical axis of the right eyeball is calculated by using a pair of two cameras 22 (Camera 0, Camera 1) and the optical axis of the left eyeball is calculated by using a pair of 2 cameras 22 (Camera 2, Camera 3), those two pairs of cameras being employed from 4 cameras disposed at the sill of the glass plate 21. The camera employed is a digital camera furnished with a CMOS image sensor with a 50 mm lens and an infrared (IR) sensor.

In the experiment, the discrepancy between the optical axis and the visual axes ($\alpha_L$, $\beta_L$, $\alpha_R$, $\beta_R$) was calculated under a constraint that the inner product of each unit vector of visual axes of the left and right eyeballs is 1 after calculating the optical axes of both eyeballs under a state that a subject gazes at any one of 9 targets through a glass plate 21. Furthermore, a discrepancy between the optical axis and the visual axis was calculated by using the conventional 1 point calibration method and both results were compared.

The experimental result is shown in the table 2 below. The subjects are 3 persons. (1 male and 2 females) The search range of the value of the horizontal a of the left eye was set from −7° to 0°, the search range of the values of the horizontal a of the left eye was set from −0° to 0°, and the search range of the value of the vertical β was set from −2° to 2° for the calculation.

TABLE 2

| Participants | | $\alpha_L$ | $\beta_L$ | $\alpha_R$ | $\beta_R$ |
|---|---|---|---|---|---|
| | | Degrees | | | |
| 1 | One-point | −1.94 | −1.93 | 2.13 | 0.86 |
| | Proposed method | −1.75 | −1.98 | 1.73 | 2.00 |
| 2 | One-point | −2.13 | 1.14 | 2.51 | 1.93 |
| | Proposed method | −2.03 | 1.36 | 2.20 | 2.00 |
| 3 | One-point | −0.80 | 0.65 | 0.64 | 0.80 |
| | Proposed method | 0.0 | 0.42 | 0.50 | 0.17 |

It is known from the results in the table 2 above that the 1 point calibration method of the conventional technique (Shown as "One-point" in the table) and the automatic calibration according to the line-of-sight measurement device according to the present invention (Shown as "Proposed method" in the table) provide similar values.

According to the present invention, $\alpha_L$, $\beta_L$, $\alpha_R$, $\beta_R$ can be automatically found by gazing in the distance, however these values can be used in the case of a close gaze. It becomes possible to precisely know which meter and things like that in the vicinity are gazed at only by gazing in the distance for a while. Also, in the case of using the present invention, the situation is that the data necessary for calculating $\alpha_L$, $\beta_L$, $\alpha_R$, $\beta_R$ can be always obtained after the calibration and the calibration result can always be corrected unlike the usual line-of sight measurement devices. Because the calibration of the present invention assumes that the user gazes in the distance, the determination whether the gaze is in the distance or nearby is important. Because the optical axis of an eyeball can be obtained within an error of ±5° by the conventional method, the determination from the direction of the optical axis is possible to some extent. The determination only from the direction of the optical axis is not possible in the case where an insect rests on a glass plate. In a case of a car for example, gazing nearby for a long time is not thinkable under a certain speed. It would be possible to obtain the determination from the viewpoint of frequency where the convergence angle becomes large at a certain car speed, by obtaining a car speed.

Note that the solution cannot be obtained from the equation (8) above if the gaze is on one point in the distance. The calculation of the present invention requires the data of different directions. It is necessary to calculate $\alpha_L$, $\beta_L$, $\alpha_R$, $\beta_R$ after generating data being not disproportionately directed from one direction by clustering the time series data depending on the direction.

Embodiment 2

Next, the line-of-sight measurement device according to embodiment 2 is explained.

In the line-of-sight measurement device according to embodiment 2, the discrepancy between the optical axes and visual axes of both the left and right eyeballs can be calculated by calculating optical axes of the left and right eyeballs when at least 2 points in the distance are gazed, under a constraint condition that the visual axes (visual lines) of the left and right eyeballs of a user are in parallel by capturing the state where 2 points in the distance are gazed.

Unlike the line-of-sight measurement device in embodiment 1, constraint that each unit vector of visual axes of the left and right eyeballs are equal when an automatic calibration is conducted by gazing 2 points in the distance.

Namely, the equation (10) holds. Here, $c_L$ and $c_R$ are unit vectors of the visual axes of the left and right eyeballs, respectively, and $\alpha_L$, $\beta_L$, $\alpha_R$, $\beta_R$ expressed the discrepancy between the optical axes and visual axes of an eyeball, each corresponding to the discrepancy in horizontal and vertical directions of the left eye and to the discrepancy in horizontal and vertical directions of the right eye, respectively.

(Equation 12)

$$c_{L0}(\alpha_L,\beta_L) = c_{R0}(\alpha_R,\beta_R)$$

$$c_{L1}(\alpha_L,\beta_L) = c_{R1}(\alpha_R,\beta_R) \quad (10)$$

The constraint that each unit vector of visual axes of the left and right eyeballs are equal is equivalent to a constraint condition that the visual axes (line-of-sight axes) of both left and right eyeballs are in parallel.

INDUSTRIAL APPLICATION POSSIBILITY

This invention is useful as a line-of-sight measurement device and a line-of-sight measurement method for operators of trains, cars, ships and so on and users who gaze in the distance from an observation platform.

EXPLANATION OF SIGNS

1 Line of sight
10 Light source means
12 Camera means
14 Optical axis calculation means
16 Discrepancy calculation means
18 Gaze point calculation means
20 Subject
21 Glass plate
22 Camera 23 Infrared LED
24 Marker for 1 point calibration
100 Line-of-sight measurement device

The invention claimed is:

1. A line-of-sight measurement device for use when a user gazes mainly at a distance, the user having a left eyeball and a right eyeball, the device comprising:
   a CPU;
   at least one light source in operational communication with the CPU;
   at least one camera in operational communication with the CPU;
   at least one program storage hardware component in operable communication with the CPU and storing at least a portion of a line-of-sight measurement program, the line-of-sight measurement program upon execution by the CPU performing a method that includes
   (a) calculating optical axes of both left and right eyeballs when at least two points at a distance of at least two meters away are being gazed upon;
   (b) calculating a discrepancy between the optical axis of the left eyeball and a visual axis of the left eyeball, and a discrepancy between the optical axis of right eyeball and a visual axis of the right eyeball, under a constraint that visual axes equivalent to lines-of-sight of both left and right eyeballs are parallel when a distant place is being gazed at; and
   (c) calculating a gazing point of said user based on a discrepancy between an optical axis and a visual axis;
   wherein said calculating optical axes includes acquiring an eyeball image including an image of an eyeball regarding a user in an occasion of gazing in the distance, and calculating an optical axis which connects a corneal curvature center or an eyeball rotation center and a pupil center of a pupil from said eyeball image.

2. A line-of-sight measurement device as set forth in claim 1, wherein said constraint condition applies with each unit vector of visual axes of both left and right eyeballs being equal.

3. A line-of-sight measurement device as set forth in claim 1, wherein:
   said optical axis calculation calculates optical axes of both left and right eyeballs when at least four points in the distance are being gazed at; and
   said constraint condition applies with an outer product value of each vector of visual axes of both the left and right eyeballs being 0 or an inner product of each unit vector of visual axes of left and right eyeballs being 1.

4. A line-of-sight measurement device as set forth in claim 3, wherein said constraint condition satisfies an equation #1 below against optical axes of both left and right eyeballs when at least four points in the distance are being gazed in a case where the inner product of unit vector of each visual axis of both left and right eyeballs is 1, equation #1 being:

$$c_{Ln}(\alpha_L,\beta_L) \cdot c_{Rn}(\alpha_R,\beta_R)=1,$$

with $c_{Ln}(\alpha_L, \beta_L)$, $c_{Rn}(\alpha_R, \beta_R)$ each being a unit vector of visual axes of each left and right eyeball, also being expressed as a function of horizontal discrepancy angle $\alpha$ and vertical discrepancy angle $\beta$, L denoting left and R denoting right, with n being 0, 1, . . . , N, and N being more than 3.

5. A line-of-sight measurement device as set forth in claim 3, wherein said constraint condition satisfies an equation #2 below against optical axes of both left and right eyeballs when at least four points in the distance are being gazed in a case where the outer product value of unit vector of each visual axis of both left and right eyeballs is 0, equation #2 being:

$$\|c_{Ln}(\alpha_L,\beta_L) \times c_{Rn}(\alpha_R,\beta_R)\|=0,$$

with $c_{Ln}(\alpha_L, \beta_L)$, $c_{Rn}(\alpha_R, \beta_R)$ each being a unit vector of visual axes of each left and right eyeball, also being expressed as a function of horizontal discrepancy angle $\alpha$ and vertical discrepancy angle $\beta$, L denoting left and R denoting right, with n being 0, 1, . . . , N, and N being more than 3.

6. A line-of-sight measurement device as set forth in claim 1, wherein said eyeball image includes an eyeball image from reflected light out of a specified light source.

7. A line-of-sight measurement device as set forth in claim 1, further comprising:
   at least two cameras, each camera disposed at a different position for acquiring eyeball images of both left and right eyeballs;
   at least two light sources, each light source disposed at a different position so that reflected light source images at eyeballs are separated from each other;
   and wherein responsive to these cameras and light sources at least two Purkinje images are formed within a region of a constant corneal curvature radius of both left and right eyeballs, and a position of a Purkinje image of the light source on the eyeball image is filmed by either one of the cameras and a position of each light source is made to correspond to each camera and the optical axis of an eyeball is calculated from the positional relationship of at least two sets of camera and corresponding light source.

8. A line-of-sight measurement device as set forth in claim 1, wherein for said discrepancy calculation, a search range of visual axes discrepancy angle against optical axes of both left and right eyeballs is constrained to be less than ±7° horizontally and less than ±2° vertically so that the discrepancy angle converges.

9. A line-of-sight measurement device as set forth in claim 1, wherein said user is an operator of at least one of: a train, a car, a ship, another transfer vehicle.

10. A line-of-sight measurement device as set forth in claim 1, wherein calculating optical axes of both left and right eyeballs is performed when at least two points at a distance of at least eight meters away are being gazed upon.

11. A line-of-sight measurement device as set forth in claim 1, wherein calculating optical axes of both left and right eyeballs is performed when at least two points at a distance of at least several meters away are being gazed upon.

12. A line-of-sight measurement device as set forth in claim 1, wherein calculating optical axes of both left and right eyeballs is performed when at least two points in a far away distance are being gazed upon.

13. A line-of-sight measurement device as set forth in claim 1, wherein said user gazes in a long distance from an observation platform.

14. A line-of-sight measurement method involving a user who gazes mainly in the distance, the user having a left eyeball and a right eyeball, the method comprising:
   calculating with a computing device having a processor optical axes of left and right eyeballs of the user when at least two points at a distance of at least eight meters away are being gazed at by the user;
   calculating with the computing device a discrepancy between the optical axis of the left eyeball and a visual axis of the left eyeball, and calculating a discrepancy between the optical axis of the right eyeball and a visual axis of the right eyeball, under a constraint that visual axes of both left and right eyeballs are parallel when the distance is being gazed at; and calculating with the computing device a gaze point of said user based on at least one of the discrepancies;

wherein calculating optical axes comprises acquiring an eyeball image including an image of an eyeball as the user gazes into the distance, and calculating an optical axis which connects a corneal curvature center or an eyeball rotation center and a pupil center of a pupil from said eyeball image.

15. A line-of-sight measurement method as set forth in claim 14, wherein calculating optical axes of both left and right eyeballs occurs when at least four points in the distance are being gazed at by the user, and either the outer product value of each vector of visual axes of both left and right eyeballs is 0 or the inner product of each unit vector of visual axes of both left and right eyeballs is 1.

16. A line-of-sight measurement device comprising:
 a CPU;
 at least one program storage hardware component in operable communication with the CPU and storing at least a portion of a line-of-sight measurement program, the line-of-sight measurement program upon execution by the CPU performing a method that includes calculating an optical axis of each of a user's left and right eyeballs when the user is gazing at two or more points which are at a distance at least eight meters away from the user, calculating a left discrepancy between the optical axis of the left eyeball and a visual axis of the left eyeball, calculating a right discrepancy between the optical axis of right eyeball and a visual axis of the right eyeball, said calculations occurring under a constraint that visual axes of the left and right eyeballs are parallel when gazing at a distant point, and calculating a gaze point of said user based on at least one discrepancy between an optical axis and visual axis;
 at least two cameras, each camera disposed at a different position, each camera position acquisition of eyeball images of both left and right eyeballs; and
 at least two light sources, each light source disposed at a different position so that reflected light source images are separated from each other.

17. A line-of-sight measurement device as set forth in claim 16, wherein said optical axis calculation includes calculating optical axes of both left and right eyeballs when at least four points in the distance are being gazed at, and said calculations occurring under a constraint that an outer product value of each vector of visual axes of both left and right eyeballs is 0 or that an inner product of each unit vector of visual axes of both left and right eyeballs is 1.

* * * * *